US012329479B2

(12) United States Patent
Riding et al.

(10) Patent No.: US 12,329,479 B2
(45) Date of Patent: Jun. 17, 2025

(54) SYSTEMS AND METHODS FOR SETTING AN IMPLANT

(71) Applicant: Warsaw Orthopedic, Inc., Warsaw, IN (US)

(72) Inventors: Shane Lars Riding, Bartlett, TN (US); Julien J. Prevost, Memphis, TN (US); Jonathan M. Dewey, Memphis, TN (US); Gregory Thomas Poulter, Zionsville, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 335 days.

(21) Appl. No.: 17/976,654

(22) Filed: Oct. 28, 2022

(65) Prior Publication Data

US 2024/0138939 A1 May 2, 2024

(51) Int. Cl.
| | | |
|---|---|---|
| *A61B 34/32* | (2016.01) | |
| *A61B 17/70* | (2006.01) | |
| *A61B 34/20* | (2016.01) | |
| *A61B 90/00* | (2016.01) | |
| *A61B 34/10* | (2016.01) | |

(52) U.S. Cl.
CPC .......... *A61B 34/32* (2016.02); *A61B 17/7082* (2013.01); *A61B 34/20* (2016.02); *A61B 90/37* (2016.02); *A61B 2034/107* (2016.02)

(58) Field of Classification Search
CPC ...................................................... A61B 34/32
See application file for complete search history.

(56) References Cited

U.S. PATENT DOCUMENTS

| | | | | |
|---|---|---|---|---|
| 8,048,115 | B2 * | 11/2011 | Winslow | A61B 17/7046 606/104 |
| 2005/0045353 | A1 * | 3/2005 | Kawai | B25B 21/02 173/183 |
| 2006/0243464 | A1 * | 11/2006 | Heinz | A61B 5/1071 172/322 |
| 2007/0119063 | A1 * | 5/2007 | Kim | A61B 5/1076 33/512 |
| 2012/0310247 | A1 * | 12/2012 | Hsieh | A61B 17/1626 606/80 |
| 2018/0325608 | A1 | 11/2018 | Kang et al. | |
| 2020/0281608 | A1 | 9/2020 | Sharifi-Mehr et al. | |

FOREIGN PATENT DOCUMENTS

| | | | |
|---|---|---|---|
| EP | 2502594 | 9/2012 | |
| EP | 4014914 | 6/2022 | |
| EP | 4014914 A1 * | 6/2022 | ......... A61B 17/7002 |
| WO | WO 2015/029042 | 3/2015 | |
| WO | WO 2020/171854 | 8/2020 | |
| WO | WO 2022/149136 | 7/2022 | |

OTHER PUBLICATIONS

International Search Report and Written Opinion for International (PCT) Patent Application No. PCT/IB2023/060623, dated Jan. 12, 2024, 14 pages.

\* cited by examiner

*Primary Examiner* — Christian A Sevilla
(74) *Attorney, Agent, or Firm* — Sheridan Ross P.C.

(57) ABSTRACT

Systems and methods for setting an implant are provided. A robotic arm may automatically orient a screw head to a predetermined orientation relative to a pedicle screw. The screw head may be pivotably coupled to the pedicle screw. The robotic arm may lock the screw head in the predetermined position.

20 Claims, 4 Drawing Sheets

SYSTEMS AND METHODS FOR SETTING AN IMPLANT

BACKGROUND

The present disclosure is generally directed to controlling one or more surgical tools, and relates more particularly to controlling one or more surgical tools to orient and lock a pedicle screw head of a pedicle screw.

Surgical robots may assist a surgeon or other medical provider in carrying out a surgical procedure, or may complete one or more surgical procedures autonomously. Providing controllable linked articulating members allows a surgical robot to reach areas of a patient anatomy during various medical procedures.

BRIEF SUMMARY

Example aspects of the present disclosure include:

A system for setting an implant according to at least one embodiment of the present disclosure comprises a processor; and a memory storing data for processing by the processor, the data, when processed, causes the processor to: cause a robotic arm to automatically orient a screw head to a predetermined orientation relative to a pedicle screw, the screw head pivotably coupled to the pedicle screw; and cause the robotic arm to lock the screw head in the predetermined orientation.

Any of the aspects herein, wherein the memory stores further data for processing by the processor that, when processed, causes the processor to plan a position of the pedicle screw to yield a predetermined position and an orientation of the screw head relative to the pedicle screw to yield the predetermined orientation.

Any of the aspects herein, wherein the memory stores further data for processing by the processor that, when processed, causes the processor to: cause the robotic arm to drive the pedicle screw to a predetermined position in an anatomical element; and cause the robotic arm to pivotably couple the screw head to the pedicle screw.

Any of the aspects herein, wherein the pedicle screw and the screw head are pivotably coupled together, and wherein the memory stores further data for processing by the processor that, when processed, causes the processor to: cause the robotic arm to drive the pedicle screw to a predetermined position in an anatomical element.

Any of the aspects herein, wherein driving the pedicle screw, orienting the screw head, and locking the screw head are performed by a single tool.

Any of the aspects herein, wherein the pedicle screw comprises a plurality of pedicle screws, the predetermined position comprises a corresponding plurality of predetermined positions, and the screw head comprises a plurality of corresponding screw heads, and wherein the robotic arm drives each pedicle screw of the plurality of pedicle screws to a corresponding predetermined position of the plurality of predetermined positions, and wherein the robotic arm orients and locks a corresponding screw head of the plurality of screw heads to the pedicle screw at a corresponding predetermined orientation.

Any of the aspects herein, wherein the memory stores further data for processing by the processor that, when processed, causes the processor to receive a surgical plan comprising at least the predetermined orientation.

Any of the aspects herein, further comprising a navigation system configured to track an orientation of the screw head and wherein the memory stores further data for processing by the processor that, when processed, causes the processor to cause the navigation system to track the orientation of the screw head and validate the orientation of the screw head with the predetermined orientation.

Any of the aspects herein, wherein the memory stores further data for processing by the processor that, when processed, causes the processor to cause the navigation system to display an image of the screw head and the orientation of the screw head on a display.

Any of the aspects herein, further comprising an arm guide, and wherein the memory stores further data for processing by the processor that, when processed, causes the processor to receive a tool through the arm guide, and wherein the robotic arm operates the tool to orient and lock the screw head.

A system for setting an implant according to at least one embodiment of the present disclosure comprises a robotic arm configured to orient a pedicle screw and a screw head; a processor; and a memory storing data for processing by the processor, the data, when processed, causes the processor to: cause the robotic arm to drive the pedicle screw to a predetermined position in an anatomical element; cause the robotic arm to automatically orient the screw head to a predetermined orientation relative to the pedicle screw, the screw head pivotably coupled to the pedicle screw; and cause the robotic arm to lock the screw head in the predetermined orientation.

Any of the aspects herein, wherein the memory stores further data for processing by the processor that, when processed, causes the processor to plan a position of the screw to yield a predetermined position and an orientation of the screw head relative to the pedicle screw to yield the predetermined orientation.

Any of the aspects herein, wherein driving the pedicle screw, orienting the screw head, and locking the screw head are performed by a single tool.

Any of the aspects herein, wherein the pedicle screw comprises a plurality of pedicle screws, the predetermined position comprises a corresponding plurality of predetermined positions, and the screw head comprises a plurality of corresponding screw heads, and wherein the robotic arm drives each pedicle screw of the plurality of pedicle screws to a corresponding predetermined position of the plurality of predetermined positions, and wherein the robotic arm orients and locks a corresponding screw head of the plurality of screw heads to the pedicle screw in a corresponding predetermined position.

Any of the aspects herein, further comprising an arm guide, and wherein the memory stores further data for processing by the processor that, when processed, causes the processor to receive a tool through the arm guide, and wherein the robotic arm operates the tool to orient and lock the screw head.

A system for setting an implant according to at least one embodiment of the present disclosure comprises a pedicle screw; a screw head configured to pivotably couple to the pedicle screw; a robotic arm configured to orient and lock the screw head in a predetermined orientation relative to the pedicle screw; a processor; and a memory storing data for processing by the processor, the data, when processed, causes the processor to: cause the robotic arm to drive the pedicle screw to a predetermined position in an anatomical element;

cause a robotic arm to automatically orient the screw head to a predetermined orientation relative to the pedicle screw, the screw head pivotably coupled to the pedicle screw; and cause the robotic arm to lock the screw head in the predetermined orientation.

Any of the aspects herein, wherein the memory stores further data for processing by the processor that, when processed, causes the processor to plan a position of the screw to yield a predetermined position and an orientation of the screw head relative to the pedicle screw to yield the predetermined orientation.

Any of the aspects herein, wherein the pedicle screw comprises a plurality of pedicle screws, the predetermined position comprises a corresponding plurality of predetermined positions, and the screw head comprises a plurality of corresponding screw heads, and wherein the robotic arm drives each pedicle screw of the plurality of pedicle screws to a corresponding predetermined position of the plurality of predetermined positions, and wherein the robotic arm orients and locks a corresponding screw head of the plurality of screw heads to the pedicle screw.

Any of the aspects herein, wherein driving the pedicle screw, orienting the screw head, and locking the screw head are performed by a single tool.

Any of the aspects herein, further comprising an arm guide, and wherein the memory stores further data for processing by the processor that, when processed, causes the processor to receive a tool through the arm guide, and wherein the robotic arm operates the tool to orient and lock the screw head.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Pedicle screw implants are used to adjust or correct various spinal deformities. The pedicle screws may be installed into one or more vertebrae of a patient and a rod may be inserted into a pedicle screw head of each of the pedicle screws. The rod essentially connects the pedicle screws and when secured to the pedicle screws, can adjust the patient's spine. Pedicle screw heads are conventionally in a fixed position relative to the pedicle screw or can be positioned in a fixed number of orientations relative to the pedicle screw. In instances where the pedicle screw head can be adjusted relative to the pedicle screw, manually orienting and locking of the pedicle screw head may be difficult due to obstructed visibility of the work volume to a user such as a surgeon or other medical provider's and/or due to the inability of the user to accurately orient and lock the pedicle screw head in a precise orientation.

According to at least one embodiment of the present disclosure, a robotic system having a robot and a robotic arm can be used to precisely orient and lock the pedicle screw head. Such precision enables preplanning of an orientation of the pedicle screw head similar to planning a position of a pedicle screw. Thus, in some instances, a position of a plurality of pedicle screws can be planned and an orientation of a corresponding plurality of pedicle screw heads can also be planned. During a surgical procedure to install the pedicle screw implants (whether during an MIS or an open procedure), the pedicle screws can be placed in corresponding anatomical elements (e.g., vertebrae) and the corresponding pedicle screw heads can be oriented and locked in a corresponding predetermined orientation. Thus, the pedicle screw head may be accurately oriented and locked in a desired orientation, thereby potentially decreasing the surgical procedure time, as the pedicle screw heads will not need to be readjusted or readjustments will be reduced.

Embodiments of the present disclosure provide technical solutions to one or more of the problems of (1) accurately orienting and locking a pedicle screw head at a predetermined orientation relative to a pedicle screw, (2) preplanning one or more orientations for one or more pedicle screw heads, and (3) decreasing surgical operating time and increasing patient safety.

Figure 1:
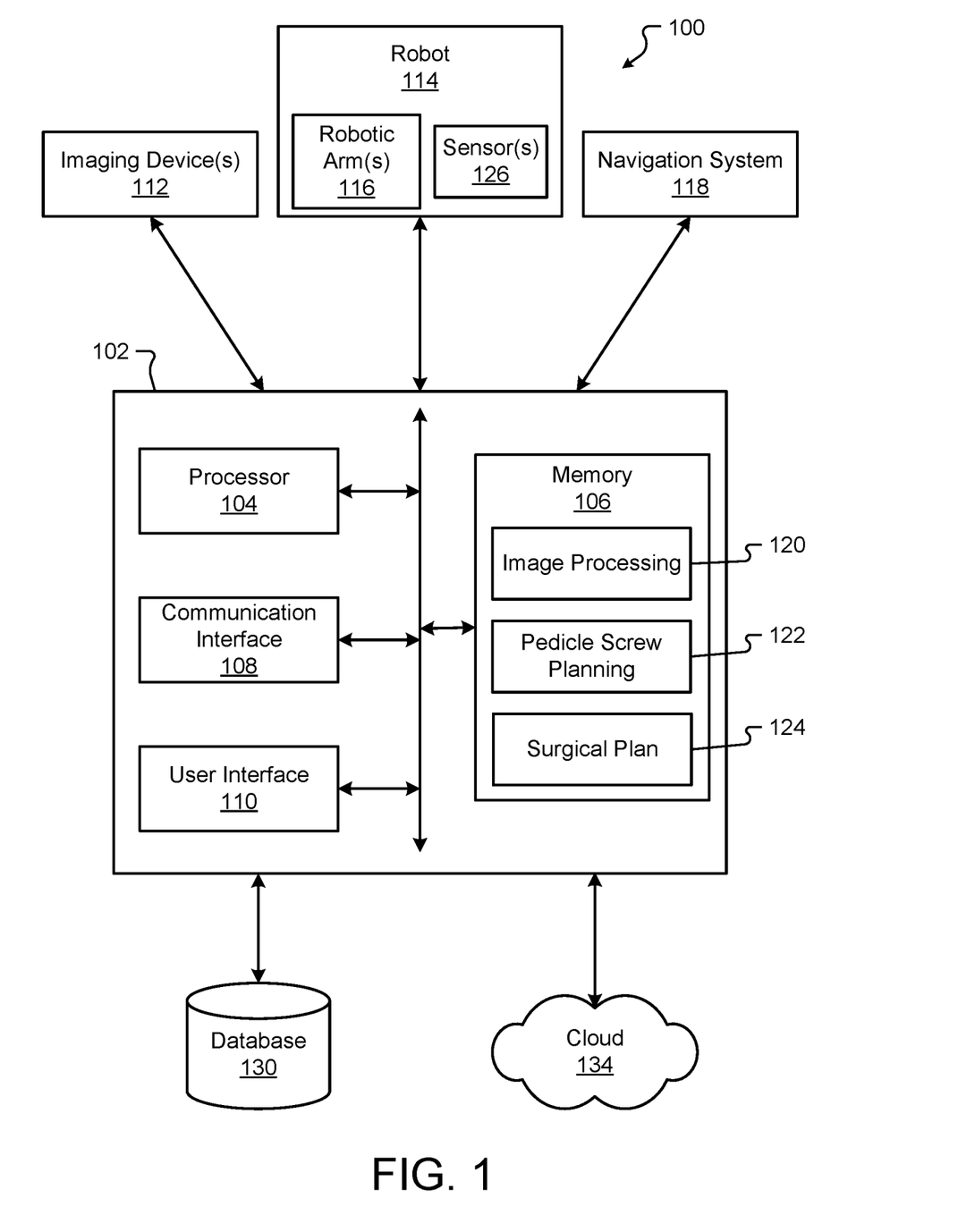
FIG. 1 is a block diagram of a system according to at least one embodiment of the present disclosure.

Turning first to FIG. 1, a block diagram of a system 100 according to at least one embodiment of the present disclosure is shown. The system 100 may be used to control one or more surgical tools to set an implant using a robotic system, e.g., control, pose, and/or otherwise manipulate a surgical robotic system, a surgical robotic arm, and/or surgical tools attached thereto and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 300 and/or 400 described herein, or of any other methods. The memory 106 may store, for example, instructions and/or machine learning models that support one or more functions of the robot 114. For instance, the memory 106 may store content (e.g., instructions and/or machine learning models) that, when executed by the processor 104, enable image processing 120 and/or pedicle screw planning 122. Such content, if provided as in instruction, may, in some embodiments, be organized into one or more applications, modules, packages, layers, or engines.

The image processing 120 enables the processor 104 to process image data of an image (received from, for example, the imaging device 112, an imaging device of the navigation system 118, or any imaging device) for the purpose of, for example, identifying information about an anatomical element such as an anatomical element 240 and/or objects such as a pedicle screw 236 and a pedicle screw head 238 depicted in the image. The information may comprise, for example, identification of hard tissue and/or soft tissues, a boundary between hard tissue and soft tissue, a boundary of hard tissue and/or soft tissue, identification of the pedicle screw 236 and the pedicle screw head 238, etc. The image processing 120 may, for example, identify hard tissue, soft tissue, and/or a boundary of the hard tissue and/or soft tissue by determining a difference in or contrast between colors or grayscales of image pixels. For example, a boundary between the hard tissue and the soft tissue may be identified as a contrast between lighter pixels and darker pixels. The image processing 120 may also be used to obtain pose information of the pedicle screw 236, the pedicle screw head 238, and/or the anatomical element 240 for the purpose of, for example, confirming a pose of the pedicle screw head 238 relative to the pedicle screw 236.

The pedicle screw planning 122 enables the processor 104 to receive information about a desired alignment of a patient's spine and generate one or more predetermined positions for the pedicle screw 236 and one or more predetermined orientations for the pedicle screw head 238. The information about the desired alignment of the patient's spine may include dimensions of the desired shape and/or a three-dimensional model of the desired alignment. The predetermined positions and/or the predetermined orientations may be transmitted directly to, for example, the robot 114 and/or stored in the surgical plan 124, the database 130, the memory 106, or any memory of any component. The pedicle screw planning 122 may output a desired orientation of the pedicle screw head based on the information. In some embodiments, the desired orientation of the pedicle screw head may be based on an alignment of a rod slot of the pedicle screw head and a rod. The desired orientation may also be based on placing the pedicle screw head perpendicular to the rod as this will result in increased strength of the connection between the pedicle screw head and the rod. It will also be appreciated that the rod slot of the pedicle screw head may be in any rotational orientation (e.g., from superior to inferior or medial to lateral) at the desired orientation of the pedicle screw head. The pedicle screw planning 122 may also output steps to orient and lock the pedicle screw head at the desired orientation. Such steps may be performed automatically by, for example, the robot 114 and/or a robotic arm 116 of the robot 114 or may be performed manually by, for example, a surgeon or other medical provider.

The memory 106 may also store a surgical plan 124. The surgical plan 124 may comprise, for example, one or more steps for performing a surgical procedure and/or one or more parameters during the surgical procedure. In some embodiments, the surgical procedure may be a spinal procedure (e.g., a spinal alignment, installing implants, osteotomy, fusion, and/or any other spinal procedure) to correct a spinal deformity. For example, the surgical plan 124 may comprise one or more surgical steps for installing and setting an implant such as preparing an anatomical element (e.g., a vertebra), drilling the anatomical element, tapping the anatomical element, decortication of the anatomical element, driving a pedicle screw 236 into the anatomical element, setting the pedicle screw head 238 to a predetermined orientation, and locking the pedicle screw head 238 in the predetermined orientation. The surgical plan 124 may also be stored in the database 130.

Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.), objects such as the pedicle screw 236 and the pedicle screw head 238, and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the pedicle screw 236 at one or more precise position(s) and orientation(s) (whether based on guidance from the navigation system 118 or not), and/or to orient the pedicle screw head 238 at a predetermined orientation relative to the pedicle screw 236. In some embodiments, the robot 114 may be configured to orient and/or operate a surgical tool such as the surgical tool 234 (which may be used to position the pedicle screw 236 and/or orient the pedicle screw head 238) and/or hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the pedicle screw 236 and/or the pedicle screw head 238. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, the pedicle screw 236, the pedicle screw head 238, the surgical tool 234, or other object held by the robot 114 (or, more specifically, by the robotic arm 116) may be precisely positionable in one or more needed and specific positions and orientations.

The robotic arm(s) 116 may comprise one or more sensors 126 that enable the processor 104 (or a processor of the robot 114) to determine a precise pose in space of the robotic arm (as well as any object such as the pedicle screw head 238 or element held by or secured to the robotic arm).

The sensor 126 may be a position sensor, a proximity sensor, a magnetometer, or an accelerometer. In some embodiments, the sensor 126 may be a linear encoder, a rotary encoder, or an incremental encoder. In still other embodiments, the sensor 126 may be an imaging sensor. Other types of sensors may also be used as the sensor 126. For example, the sensor 126 may be a force sensor, configured to detect a force applied on the robotic arm 116 (e.g., whether via an end effector of the robotic arm 116, a tool held by an end effector of the robotic arm 116, or otherwise). The one or more sensors 126 may be positioned, for example, on the robotic arm 116 or elsewhere.

Data from the sensor(s) 126 may be provided to a processor of the robot 114, to the processor 104 of the computing device 102, and/or to the navigation system 118. The data may be used to calculate a position in space of the robotic arm 116 relative to one or more coordinate systems (e.g., based on coordinate system information stored in the memory 116). The calculation may be based not just on data received from the sensor(s) 126, but also on data or information (such as, for example, physical dimensions) about, for example, the robot 114 or a portion thereof, or any other relevant object, which data or information may be stored, for example, in a memory 116 of a computing device 102 or in any other memory.

In some embodiments, reference markers (e.g., navigation markers) may be placed on the robot 114 (including, e.g., on the robotic arm 116), the imaging device 112, the surgical tool 234, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (e.g., a pose) of the imaging device 112, the robot 114 and/or robotic arm 116, and/or one or more surgical tools 234 (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, the one or more surgical plans 124 (including, for example, one or more predetermined positions for one or more pedicle screws 236, one or more predetermined orientations for one or more pedicle screw heads 238, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods 300 and/or 400 described herein. The system 100 or similar systems may also be used for other purposes.

Figure 2:
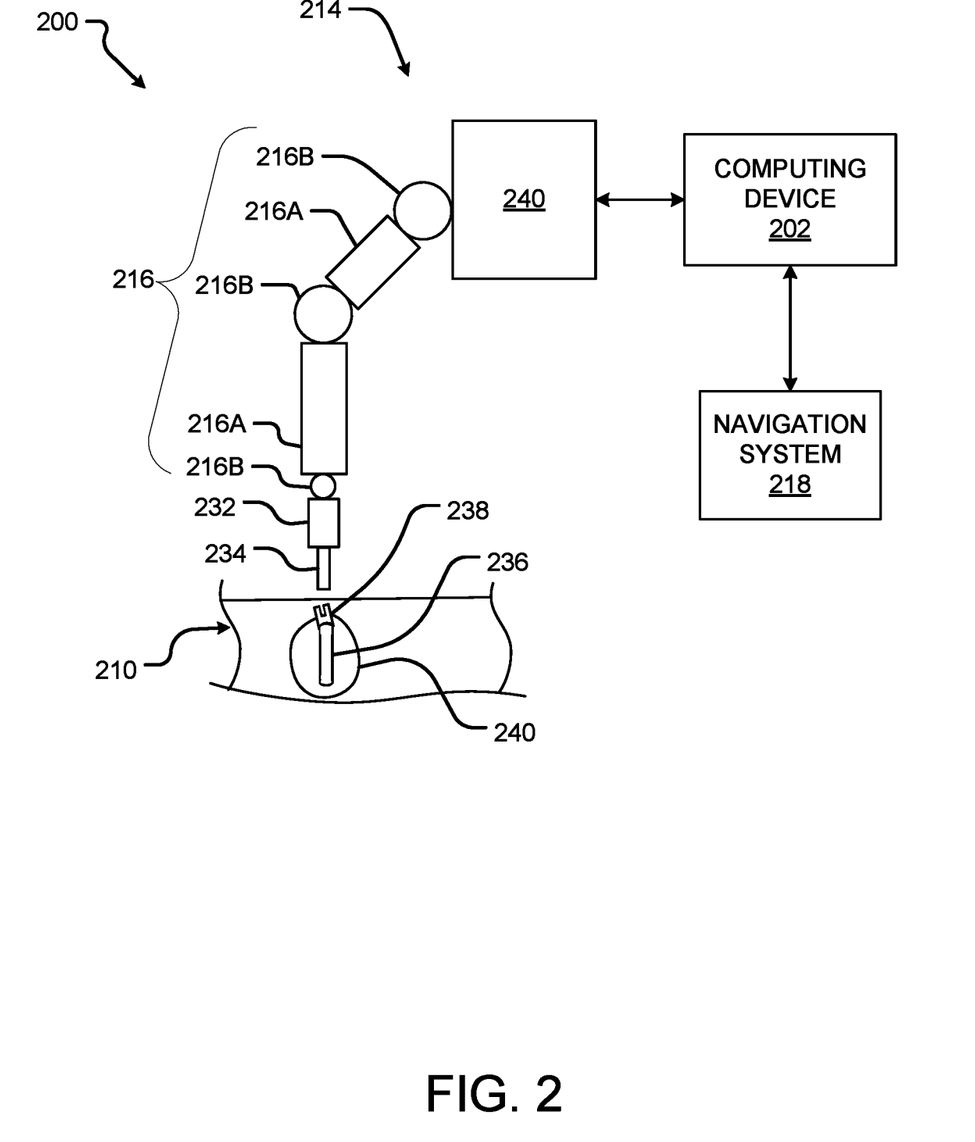
FIG. 2 is a block diagram of a system according to at least one embodiment of the present disclosure.

Turning to FIG. 2 a block diagram of a system 200 according to at least one embodiment of the present disclosure is shown. The system 200 includes a computing device 202 (which may be the same as or similar to the computing device 102 described above), a navigation system 218 (which may be the same as or similar to the navigation system 118 described above), and a robot 214 (which may be the same as or similar to the robot 114 described above). The system 200 may be used with the system 100 in some embodiments. Systems according to other embodiments of the present disclosure may comprise more or fewer components than the system 200. For example, the system 200 may not include the navigation system 218.

As illustrated, the robot 214 includes a robotic arm 216 (which may comprise one or more members 216A connected by one or more joints 216B) extending from a base 240. The base 240 may be stationary or movable. In some embodiments, the robot 214 may include one robotic arm or two or more robotic arms. In embodiments where the robot 214 includes more than two robotic arms, the robotic arms may operate in a shared or common coordinate space. By operating in the common coordinate space, the robotic arms avoid colliding with each other during use, as a position of each robotic arm is known to each other.

In some embodiments, an arm guide 232 and the surgical tool 234 (which may be used for, for example, positioning the pedicle screw 236 and orienting the pedicle screw head 238) may be disposed or supported on an end of the robotic arm 216. In other embodiments, the arm guide 232 and the surgical tool 234 be disposed or secured to any portion of the robotic arm 216. In other embodiments, any one or more tool(s), instrument(s), or component(s) may be supported by, secured to, or disposed on a robotic arm. The robotic arm 216 is operable to execute one or more planned movements and/or procedures autonomously and/or based on input from a surgeon or user.

As illustrated in FIG. 2, the surgical tool 234 is supported by the robotic arm 216. The surgical tool 234 may be used to perform an action or a procedure on a patient 210 and/or to position the pedicle screw 236 and/or the pedicle screw head 238 whether based on instructions from a surgeon and/or pursuant to a surgical plan such as the surgical plan 124. For example, the surgical tool 234 may be used to install an implant such as the pedicle screw 236 and the pedicle screw head 238 in the patient 210 by performing one or more steps such as preparing the anatomical element 236 (e.g., a vertebra), drilling the anatomical element 236, tapping the anatomical element 236, decortication of the anatomical element 236, driving the pedicle screw 236 into the anatomical element 236, orienting the pedicle screw 236 at a predetermined orientation, and locking the pedicle screw head 238 at the predetermined orientation.

The pedicle screw 236 and the pedicle screw head 238 may be pivotably coupled to each other such that the pedicle screw head 238 can be moved or rotated about the pedicle screw 236 and positioned in any orientation. In conventional surgical procedures, it may be difficult to manually set the pedicle screw head 238 at a precise orientation and it may also be difficult to manually lock the pedicle screw head 238 at the desired orientation. The robotic arm 116 advantageously enables precise positioning and locking of the pedicle screw head 238 at the desired orientation, thus increasing success of a surgical outcome.

Figure 3:
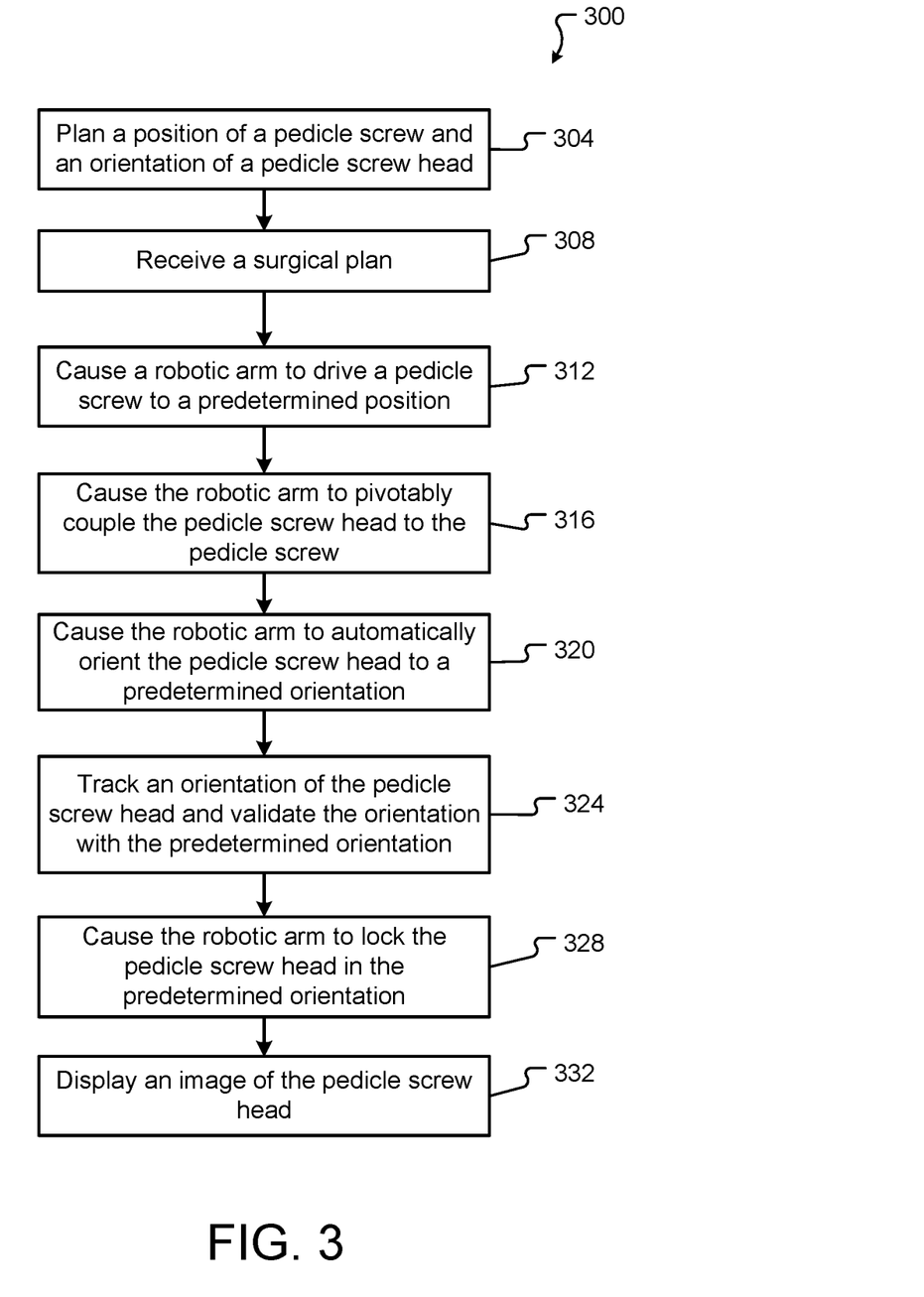
FIG. 3 is a flowchart according to at least one embodiment of the present disclosure.

FIG. 3 depicts a method 300 that may be used, for example, for controlling one or more surgical tools such as the surgical tool 234 to position an implant such as the pedicle screw 236 and to orient and/or lock a pedicle screw head such as the pedicle screw head 238. It will be appreciated that though the method 300 is described with respect to setting and locking a pedicle screw 236 and a pedicle screw head 238, the method 300 can be used to set, position, orient, place, lock, and/or install any implant.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing elements stored in a memory such as the memory 106. The elements stored in memory and executed by the processor may cause the processor to execute one or more steps of a function as shown in method 300. One or more portions of a method 300 may be performed by the processor executing any of the contents of memory, such as an image processing 120 and/or a pedicle screw planning 122.

The method 300 comprises planning a position of a pedicle screw and an orientation of a pedicle screw head (step 304). The position and the orientation may be planned using a processor such as the processor 104 executing a pedicle screw planning such as the pedicle screw planning 122. As previously described, the pedicle screw planning enables the processor to receive information about a desired alignment of a patient's spine and generate one or more predetermined positions for the pedicle screw (such as the pedicle screw 236) and one or more predetermined orientations for the pedicle screw head (such as the pedicle screw head 238). The information about the desired alignment of the patient's spine may include dimensions of the desired alignment and/or a three-dimensional model of the desired alignment. The predetermined positions and/or the predetermined orientations may be transmitted directly to, for example, a robot such as the robot 114 and/or stored in a surgical plan such as the surgical plan 124, a database such as the database 130, a memory such as the memory 106, or any memory of any component.

It will be appreciated that the method 300 may not include the step 304. It will also be appreciated that the planning may include planning a position for one or more pedicle screws and an orientation for one or more pedicle screw heads. The planning may also include planning a trajectory for a surgical tool such as the surgical tool 234 to position one or more pedicle screws and to orient and lock one or more pedicle screw heads.

The method 300 also comprises receiving a surgical plan (step 308). The surgical plan may be the same as or similar to the surgical plan 124. The surgical plan may comprise one or more surgical steps for installing and setting an implant such as preparing an anatomical element (e.g., a vertebra), drilling the anatomical element, tapping the anatomical element, decortication of the anatomical element, driving a pedicle screw into the anatomical element, setting the pedicle screw head to a predetermined orientation, and locking the pedicle screw head in the predetermined orientation. The surgical plan may be stored in and received from a memory such as the memory 106, a database such as the database 130, a cloud such as the cloud 134, and/or any other component of a system such as the system 100 capable of storing the surgical plan 124.

It will be appreciated that the method 300 may not include the step 308.

The method 300 also comprises causing a robotic arm to drive the pedicle screw to a predetermined position in the anatomical element (step 312). The robotic arm may be the same as or similar to the robotic arm 116 of a robot such as the robot 114. The predetermined position may be determined in, for example, the step 304 or the surgical plan may include the predetermined orientation, which may be received in the step 308. In some embodiments, the surgical tool may be used to orient and drive the pedicle screw into an anatomical element such as the anatomical element 240. The surgical tool may comprise, for example, a driver configured to rotate or drive the pedicle screw into the anatomical element. In such embodiments, the anatomical element may be a vertebra and the anatomical element may be prepared to receive the pedicle screw. For example, a bore may be drilled and tapped into the anatomical element and a portion of the anatomical element may be reamed or milled to form a cavity shaped to receive a head of the pedicle screw. In embodiments where the pedicle screw and the pedicle screw head are coupled together, the pedicle screw may then be driven into the bore and the pedicle screw head may be seated in the cavity. In embodiments where the pedicle screw and the pedicle screw head are not yet coupled together, the pedicle screw may be driven into the bore and step 316, described below, may occur.

The method 300 also comprises causing the robotic arm to pivotably couple the pedicle screw head to the pedicle screw (step 316). In some embodiments, the pedicle screw may be driven into the predetermined position in the step 312 without the pedicle screw head. In such embodiments, the robotic arm may use the surgical tool (whether the same surgical tool as the surgical tool used in the step 312 or a different surgical tool) to pivotably couple the pedicle screw head to the pedicle screw. It will be appreciated that in some embodiments, the robotic arm may comprise an arm guide such as the arm guide 232 configured to receive and guide the surgical tool. The arm guide may also be configured to prevent the surgical tool from moving past a predetermined depth in instances of, for example, drilling, tapping, reaming, driving, or any other task performed using the surgical tool.

It will be appreciated that the method 300 may not include the step 316 or the step 316 may be performed prior to the step 312. For example, in some embodiments, the pedicle screw head may be coupled to the pedicle screw prior to the start of a surgical operation. In such embodiments, the pedicle screw and the pedicle screw head may be driven together to the predetermined position.

The method 300 also comprises causing the robotic arm to automatically orient the pedicle screw head to a predetermined orientation (step 320). The predetermined orientation may be determined in, for example, the step 304 or the surgical plan may include the predetermined orientation, which may be received in the step 308. The robotic arm may use the surgical tool (which may be the same as or different from the surgical tool used in the steps 312 and/or 316) to orient the pedicle screw head to the predetermined orientation relative to the pedicle screw. As previously described, the pedicle screw and the pedicle screw head may be pivotably coupled to each other such that the pedicle screw head can be moved or rotated about the pedicle screw and set to an orientation relative to the pedicle screw.

The method 300 also comprises tracking an orientation of the pedicle screw head and validating the orientation with the predetermined orientation (step 324). The orientation of the pedicle screw head may be tracked by a navigation system such as the navigation system 118. In such embodiments, the navigation system may use imaging and/or markers to track the orientation of the pedicle screw head. In other embodiments, a pose of the robotic arm may be determined when the robotic arm has oriented the pedicle screw head at the predetermined orientation, which can be correlated to the orientation of the pedicle screw head. In other embodiments, image data from an imaging device such as the imaging device 112 may be used to determine an orientation of the pedicle screw head. The image data may be processed by the processor using an image processing such as the imaging processing 120 to identify the pedicle screw head in the image data and to determine a pose of the pedicle screw.

The orientation (as tracked by the navigation system, determined by the robotic arm and/or image processing, etc.) may be compared to the predetermined orientation to validate the actual orientation of the pedicle screw head. In some embodiments, a notification may be generated if a difference between the orientation and the predetermined orientation meets an orientation threshold. Such notification may alert or notify a user such as a surgeon or other medical provider that the pedicle screw head may need adjusting to orient the pedicle screw head at the predetermined orientation. In other instances, the notification may be generated to notify the user that the pedicle screw head is in the predetermined orientation. In other embodiments, an angle of difference between the pedicle screw head and another reference geometry such as, for example, surrounding anatomy, global anatomy (balls of hips, or another vertebral body) or the shank, could be displayed to the user (e.g., surgeon) for their knowledge and confirmation of the angle of difference.

In some instances, the pedicle screw head may be tracked to indicate when the pedicle screw head is aligned to properly receive a rod so as to avoid misalignment of the rod and a rod slot of the pedicle screw head. In such instances, a rotational orientation and an angulation of the pedicle screw head may be tracked until the pedicle screw head is aligned such that a rod slot of the pedicle screw head is aligned with the rod. The desired orientation of the pedicle screw head to align the rod slot with the rod may be planned preoperatively or intraoperatively by, for example, the processor 104 using the pedicle screw planning 122. In some embodiments the desired orientation of the pedicle screw head may be received from a surgical plan such as the surgical plan 124, from a database such as the database 130, a cloud such as the cloud 134, or from any other component.

The pedicle screw planning 112 may receive an actual orientation of the one or more pedicle screw heads and output an update alignment for a patient's spine or update a desired rod shape. In some embodiments, the pedicle screw planning 122 may also be used intraoperatively to update one or more desired orientations of one or more pedicle screw heads. For example, a pedicle screw shank can be placed into an unbroken portion of a vertebra that has an anterior column burst fracture. An angle of a pedicle screw head pivotably attached to the pedicle screw shank can be set at a desired orientation that would restore lordosis to the spine at the location of the vertebra. In such example, the pedicle screw planning 122 can output the desired orientation of the pedicle screw head based on a fixed position of a rod such that the pedicle screw head is perpendicular to the rod. In such instances, when the rod is coupled to the pedicle screw head, the vertebral body can adjust to a final, lordotic position.

It will be appreciated that in some embodiments, the method 300 may not include the step 324.

The method 300 also comprises causing the robotic arm to lock the pedicle screw head in the predetermined orientation (step 328). The robotic arm may use the surgical tool to lock the pedicle screw head in the predetermined orientation. In some instances, the robotic arm can also unlock the pedicle screw head. For example, the pedicle screw head may be reoriented to move the vertebra to which the pedicle screw is attached thereto, thereby adjusting the alignment of at least a portion of the patient's spine. In another example, the pedicle screw head may be adjusted to receive a rod.

In some embodiments, the surgical tool may be the same surgical tool for the steps 312, 316, 320, and/or 328. In other embodiments, the surgical tool may be a different surgical tool for one or more of the steps 312, 316, 320, and/or 328.

The method 300 also comprises displaying an image of the pedicle screw head (step 332). The image of the pedicle screw head may be displayed on a user interface such as the user interface 110. In some embodiments, an image of the surgical tool may also be displayed with the image of the pedicle screw head. In such embodiments, the image of the pedicle screw head may be superimposed on the image of the surgical tool. The image of the pedicle screw head may move with the image of the surgical tool to illustrate to the user that the pedicle screw head matches a planned trajectory (which may also be shown).

The image of the pedicle screw head may also show an orientation of the pedicle screw head whether as an image of the pedicle screw head relative to an image of the pedicle screw and/or by displaying a numeric value of the orientation. The user may use the image(s) displayed to confirm and/or adjust the pedicle screw head and/or pedicle screw to a desired orientation and/or position. Additionally or alternatively, the user may set the orientation of the pedicle screw head prior to locking the pedicle screw head in the orientation. In such instances, the step 332 may occur prior to or simultaneously with the step 328. It will be appreciated that in some embodiments, the user may set the pedicle screw head at an orientation intra-operatively that is different from an orientation of the pedicle screw head as defined by a surgical plan such as the surgical plan 124.

It will be appreciated that the method 300 may not comprise the step 332.

The method 300, any steps of the method 300, or any combination of the steps of the method 300 may be repeated. For example, in some embodiments, the pedicle screw may comprise a plurality of pedicle screws, the predetermined position may comprise a corresponding plurality of predetermined positions, the screw head may comprise a plurality of corresponding screw heads. In such embodiments, the robotic arm may drive each pedicle screw of the plurality of pedicle screws to a corresponding predetermined position of the plurality of predetermined positions. The robotic arm may also orient and lock a corresponding screw head of the plurality of screw heads to the pedicle screw at a corresponding predetermined orientation.

The present disclosure encompasses embodiments of the method 300 that comprise more or fewer steps than those described above, and/or one or more steps that are different than the steps described above.

Figure 4:
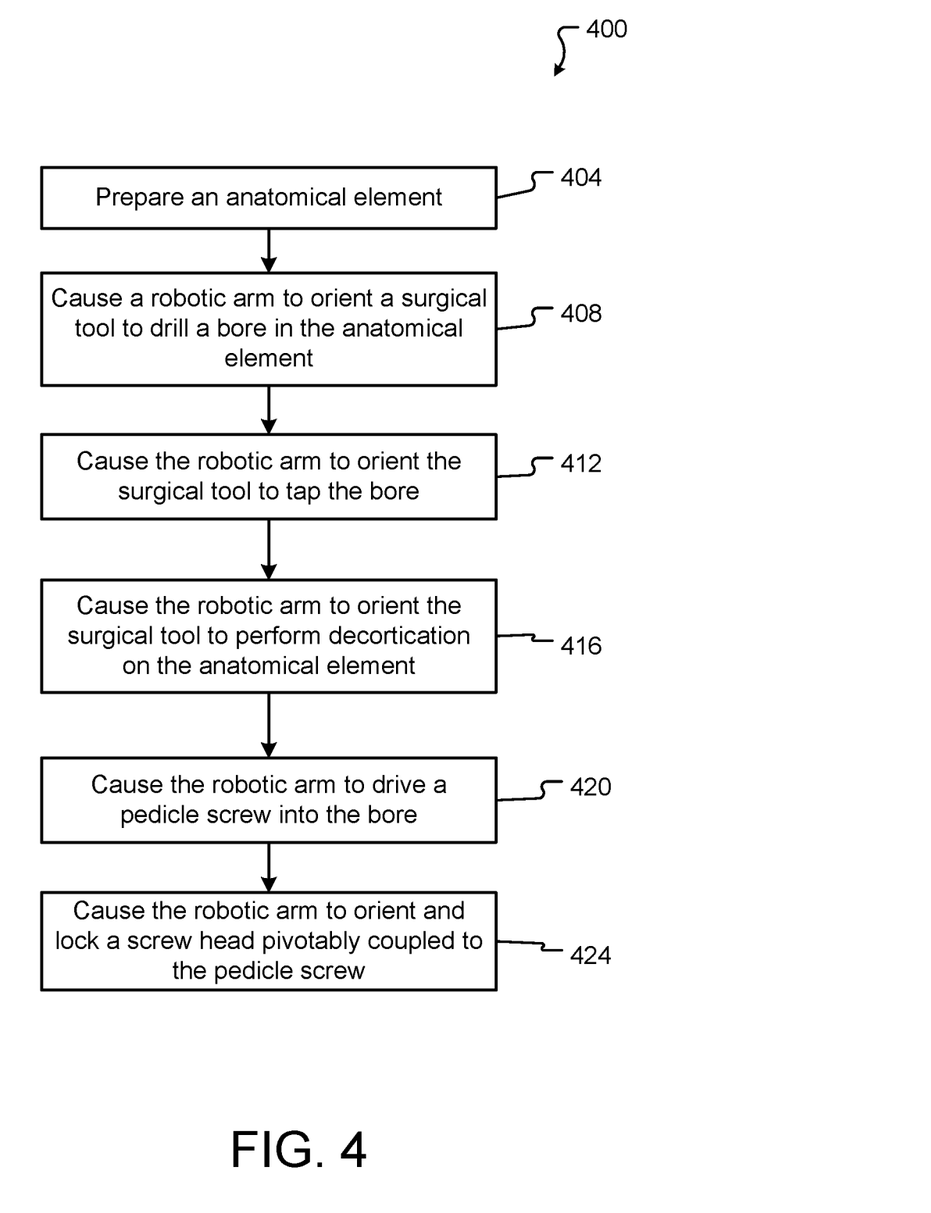
FIG. 4 is a flowchart according to at least one embodiment of the present disclosure.

FIG. 4 depicts a method 400 that may be used, for example, for controlling one or more surgical tools such as the surgical tool 234 to form prepare an anatomical element such as the anatomical element 236 for receiving an implant such as the implant 238. Though the method 400 will be described relative to installing an implant such as a pedicle screw implant, it will be appreciated that the method 400 can be used to form a custom-shaped cavity for any purpose, reason, or use.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing elements stored in a memory such as the memory 106. The elements stored in memory and executed by the processor may cause the processor to execute one or more steps of a function as shown in method 400. One or more portions of a method 400 may be performed by the processor executing any of the contents of memory, such as an image processing 120 and/or a trajectory planning 122.

The method 400 comprises preparing an anatomical element (step 404). The anatomical element may be the same as or similar to the anatomical element 236 and may comprise, for example, a vertebra. The anatomical element may be prepared to receive, for example, an implant such as the implant 238. The implant may be a pedicle screw, though in other instances the implant may be, for example, a rod, a cage, etc. Preparing the anatomical element may include scraping, polishing, marking, forming a pilot hole, or a combination thereof on a surface of the anatomical element. A surgical tool such as the surgical tool 234 may be used to prepare the anatomical element. The anatomical element may be prepared manually by a user operating the surgical tool or by a robotic arm such as the robotic 116, 216 of a robot such as the robot 114, 214 assisting the user or automatically orienting and operating the surgical tool. In some embodiments, an arm guide such as the arm guide 232 may be attached to the robotic arm and the surgical tool may be received through the arm guide. In such embodiments, the arm guide may be configured to receive the surgical tool (or any surgical tool) and prevent movement of the surgical tool past a predetermined depth. Whether the surgical tool is received by the arm guide or is otherwise coupled to the robotic arm, the surgical tool is supported, oriented, and operated by the robotic arm. As previously described, the robotic arm is capable of precisely positioning and orienting a surgical tool such as the surgical tool and is configured to orient the surgical tool along a trajectory.

The method 400 also comprises causing the robotic arm to orient the surgical tool to drill a bore in the anatomical element (step 408). The surgical tool may be the same as or similar to the surgical tool used in the step 404 to prepare the anatomical element. In other instances, the surgical tool may be a different surgical tool than the surgical tool used in the step 404. Causing the robotic arm to orient the surgical tool may include causing the robotic arm to orient the surgical tool in one direction along a first trajectory to remove the first portion of the anatomical element (e.g., drill). The first portion, in some embodiments, forms the bore in the anatomical element. In such embodiments, the first trajectory may comprise a depth for the surgical tool to drill to in the anatomical element. As previously described, the first trajectory may be obtained from, for example, a memory such as the memory 106 of a computing device such as the computing device 102, a surgical plan such as the surgical plan 124, and/or a database such as the database 130. In other instances, the first trajectory may be obtained from, for example, the processor executing a trajectory planning such as the trajectory planning 122. As previously described, the trajectory planning enables the processor to receive information about a desired custom shaped cavity and/or a desired bore and generate a trajectory for the surgical tool to remove one or more portions from the anatomical element. The one or more portions may form the bore, a custom shaped cavity, or any other shape, volume, or combinations of shapes.

The method 400 also comprises causing the robotic arm to orient the surgical tool to tap the bore (step 412). The surgical tool may be the same as or similar to the surgical tool used in the steps 404 and/or 408 to prepare the anatomical element and/or to drill the anatomical element. In other instances, the surgical tool may be a different surgical tool than the surgical tool used in the steps 404 and/or 408. Causing the robotic arm to orient the surgical tool may include causing the robotic arm to orient the surgical tool in one direction along the first trajectory to tap the bore formed in the step 408.

The method 400 also comprises causing the robotic arm to orient the surgical tool to perform decortication on the anatomical element (step 416). The step 416 may be the same as or similar to the step 316 of the method 300 described above. The surgical tool may be the same as or similar to the surgical tool used in the steps 404, 408, and/or 412 to prepare the anatomical element, to drill the anatomical element, and/or to tap the bore. In other instances, the surgical tool may be a different surgical tool than the surgical tool used in the steps 404, 408, and/or 412. Orienting the surgical tool to perform decortication may include orienting the surgical tool in at least one direction to remove a second portion of the anatomical element The at least one direction may comprise a lateral direction and depth direction. It will be appreciated that the at least one direction may comprise any direction(s). The second portion removed from the anatomical element may form a custom shaped cavity such as the custom shaped cavity 238 in the anatomical element. The custom shaped cavity in some instances may have a cross-sectional area larger than a cross-sectional area of the second surgical tool (or any surgical tool). In some embodiments, the custom shaped cavity may be shaped to receive a head of a pedicle screw implant such that the head may seat flush against the anatomical element. The custom shaped cavity enables the pedicle screw implant to have a lower profile relative to the anatomical element. Without such custom shaped cavity, the head and the pedicle screw may be left proud and exposed relative to the anatomical element.

As previously described, decortication of the anatomical element may include using the surgical tool to remove at least a portion of the anatomical element to form the custom shaped cavity. Such decortication is enabled by the robotic arm precisely operating the surgical tool in a working volume that may not be visible to a user such as the surgeon or other medical provider. In other words, the robotic arm is capable of orienting and operating the surgical tool in spaces that the user cannot view particularly in, for example, MIS procedures. Thus, cavities of complex geometries or shapes may be formed by the robotic arm operating the surgical tool in a working volume that is conventionally difficult to work within.

The method 400 also comprises causing the robotic arm to drive the pedicle screw into the bore (step 420). The step 420 may be the same as or similar to the step 328 of the method 300 described above. Causing the robotic arm to drive the pedicle screw into the bore may include the robotic arm using a surgical tool such as a screwdriver to drive the implant.

The method 400 also comprises causing the robotic arm to orient and lock a screw head pivotably coupled to the pedicle screw (424). The step 424 may be the same as or similar to the steps 320 and 328 of the method 300 described above. It will be appreciated that the steps 404, 408, 412, 416, 420, and/or 424 (e.g., preparing the anatomical element, drilling a bore in the anatomical element, tapping the bore, forming the custom-shaped cavity (e.g., decortication), driving the pedicle screw into the bore, and/or orienting and locking the screw head relative to the pedicle screw) may be performed with the same surgical tool. It will also be appreciated that the method 400 may include other steps such as, for example, preparing the anatomical element and tapping the anatomical element and in such instances any combination of steps may be performed with the same surgical tool.

The present disclosure encompasses embodiments of the method 400 that comprise more or fewer steps than those described above, and/or one or more steps that are different than the steps described above.

As noted above, the present disclosure encompasses methods with fewer than all of the steps identified in FIGS. 3 and 4 (and the corresponding description of the methods 300 and 400), as well as methods that include additional steps beyond those identified in FIGS. 3 and 4 (and the corresponding description of the methods 300 and 400). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for setting an implant comprising:
a processor; and
a memory storing data for processing by the processor, the data, when processed, causes the processor to:
cause a robotic arm to automatically orient a screw head to a predetermined orientation relative to a pedicle screw, the screw head pivotably coupled to the pedicle screw; and
cause the robotic arm to lock the screw head in the predetermined orientation.

2. The system of claim 1, wherein the memory stores further data for processing by the processor that, when processed, causes the processor to plan a position of the pedicle screw to yield a predetermined position and an orientation of the screw head relative to the pedicle screw to yield the predetermined orientation.

3. The system of claim 2, wherein the memory stores further data for processing by the processor that, when processed, causes the processor to:
cause the robotic arm to drive the pedicle screw to a predetermined position in an anatomical element; and
cause the robotic arm to pivotably couple the screw head to the pedicle screw.

4. The system of claim 2, wherein the pedicle screw and the screw head are pivotably coupled together, and wherein the memory stores further data for processing by the processor that, when processed, causes the processor to:
cause the robotic arm to drive the pedicle screw to a predetermined position in an anatomical element.

5. The system of claim 4, wherein driving the pedicle screw, orienting the screw head, and locking the screw head are performed by a single tool.

6. The system of claim 4, wherein the pedicle screw comprises a plurality of pedicle screws, the predetermined position comprises a plurality of predetermined positions, and the screw head comprises a plurality of screw heads, wherein the robotic arm drives each pedicle screw of the plurality of pedicle screws to a corresponding predetermined position of the plurality of predetermined positions, and wherein the robotic arm orients and locks a corresponding screw head of the plurality of screw heads to the pedicle screw at a corresponding predetermined orientation.

7. The system of claim 1, wherein the memory stores further data for processing by the processor that, when processed, causes the processor to receive a surgical plan comprising at least the predetermined orientation.

8. The system of claim 1, further comprising a navigation system configured to track an orientation of the screw head, wherein the memory stores further data for processing by the processor that, when processed, causes the processor to cause the navigation system to track the orientation of the screw head and validate the orientation of the screw head with the predetermined orientation.

9. The system of claim 8, wherein the memory stores further data for processing by the processor that, when processed, causes the processor to cause the navigation system to display an image of the screw head and the orientation of the screw head on a display.

10. The system of claim 1, further comprising an arm guide, wherein the memory stores further data for processing by the processor that, when processed, causes the processor to receive a tool through the arm guide, and wherein the robotic arm operates the tool to orient and lock the screw head.

11. A system for setting an implant comprising:
a robotic arm configured to orient a pedicle screw and a screw head;
a processor; and
a memory storing data for processing by the processor, the data, when processed, causes the processor to:
cause the robotic arm to drive the pedicle screw to a predetermined position in an anatomical element;
cause the robotic arm to automatically orient the screw head to a predetermined orientation relative to the pedicle screw, the screw head pivotably coupled to the pedicle screw; and
cause the robotic arm to lock the screw head in the predetermined orientation.

12. The system of claim 11, wherein the memory stores further data for processing by the processor that, when processed, causes the processor to plan a position of the pedicle screw to yield a predetermined position and an orientation of the screw head relative to the pedicle screw to yield the predetermined orientation.

13. The system of claim 11, wherein driving the pedicle screw, orienting the screw head, and locking the screw head are performed by a single tool.

14. The system of claim 11, wherein the pedicle screw comprises a plurality of pedicle screws, the predetermined position comprises a plurality of predetermined positions, and the screw head comprises a plurality of screw heads, wherein the robotic arm drives each pedicle screw of the plurality of pedicle screws to a corresponding predetermined position of the plurality of predetermined positions, and wherein the robotic arm orients and locks a corresponding screw head of the plurality of screw heads to the pedicle screw in a corresponding predetermined position.

15. The system of claim 11, further comprising an arm guide, wherein the memory stores further data for processing by the processor that, when processed, causes the processor to receive a tool through the arm guide, and wherein the robotic arm operates the tool to orient and lock the screw head.

16. A system for performing a surgical procedure comprising:
a pedicle screw;
a screw head configured to pivotably couple to the pedicle screw;
a robotic arm configured to orient and lock the screw head in a predetermined orientation relative to the pedicle screw;
a processor; and
a memory storing data for processing by the processor, the data, when processed, causes the processor to:
cause the robotic arm to drive the pedicle screw to a predetermined position in an anatomical element;
cause a robotic arm to automatically orient the screw head to a predetermined orientation relative to the pedicle screw, the screw head pivotably coupled to the pedicle screw; and
cause the robotic arm to lock the screw head in the predetermined orientation.

17. The system of claim 16, wherein the memory stores further data for processing by the processor that, when processed, causes the processor to plan a position of the pedicle screw to yield a predetermined position and an orientation of the screw head relative to the pedicle screw to yield the predetermined orientation.

18. The system of claim 16, wherein the pedicle screw comprises a plurality of pedicle screws, the predetermined position comprises a plurality of predetermined positions, and the screw head comprises a plurality of screw heads, wherein the robotic arm drives each pedicle screw of the plurality of pedicle screws to a corresponding predetermined position of the plurality of predetermined positions, and wherein the robotic arm orients and locks a corresponding screw head of the plurality of screw heads to the pedicle screw.

19. The system of claim 16, wherein driving the pedicle screw, orienting the screw head, and locking the screw head are performed by a single tool.

20. The system of claim 16, further comprising an arm guide, wherein the memory stores further data for processing by the processor that, when processed, causes the processor to receive a tool through the arm guide, and wherein the robotic arm operates the tool to orient and lock the screw head.

* * * * *